(12) United States Patent
Cunningham

(10) Patent No.: US 7,981,137 B2
(45) Date of Patent: *Jul. 19, 2011

(54) UNIFORM STRESS NEEDLE

(75) Inventor: Scott Cunningham, Cheshire, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 393 days.

This patent is subject to a terminal disclaimer.

(21) Appl. No.: 11/415,740

(22) Filed: May 1, 2006

(65) Prior Publication Data

US 2006/0195141 A1 Aug. 31, 2006

Related U.S. Application Data

(63) Continuation of application No. 10/620,160, filed on Jul. 15, 2003, now Pat. No. 7,063,716.

(60) Provisional application No. 60/396,376, filed on Jul. 17, 2002.

(51) Int. Cl.
*A61B 17/06* (2006.01)

(52) U.S. Cl. ........................................ 606/222; 606/223

(58) Field of Classification Search .................. 606/222, 606/223, 224–227
See application file for complete search history.

(56) References Cited

U.S. PATENT DOCUMENTS

| 20,409 | A | | 6/1858 | Jas |
| 461,602 | A | | 10/1891 | Boult |
| 1,599,059 | A | | 9/1926 | Morton |
| 1,648,451 | A | | 11/1927 | Fisher |
| 2,841,150 | A | * | 7/1958 | Riall .............................. 606/223 |
| 3,038,475 | A | | 6/1962 | Orcutt |
| 3,238,942 | A | | 3/1966 | Lincoff |
| 4,237,892 | A | * | 12/1980 | Ritter et al. ................... 606/223 |
| 4,513,747 | A | | 4/1985 | Smith |
| 4,524,771 | A | | 6/1985 | McGregor et al. |
| 4,660,559 | A | | 4/1987 | McGregor et al. |
| 4,799,484 | A | | 1/1989 | Smith et al. |
| 4,901,722 | A | * | 2/1990 | Noguchi ........................ 606/223 |
| 5,002,565 | A | | 3/1991 | McGregor |
| 5,100,432 | A | | 3/1992 | Matsutani |
| 5,330,441 | A | * | 7/1994 | Prasad et al. .................. 606/222 |
| 5,342,397 | A | | 8/1994 | Guido |
| 5,464,422 | A | | 11/1995 | Silverman |
| 5,476,480 | A | * | 12/1995 | Matsutani et al. ............. 606/222 |
| 5,683,416 | A | | 11/1997 | McGregor et al. |
| 5,693,071 | A | | 12/1997 | Gorecki et al. |
| 5,792,180 | A | | 8/1998 | Munoz |
| 5,797,961 | A | | 8/1998 | Smith et al. |
| 5,913,875 | A | | 6/1999 | Smith et al. |
| 6,120,517 | A | | 9/2000 | Daum et al. |

FOREIGN PATENT DOCUMENTS

EP 0 809 968 A1 12/1997
WO WO 95/01129 A1 1/1995

OTHER PUBLICATIONS

PCT Search Report.
European Search Report for EP 03764662.7-2310 date of completion is Apr. 26, 2010 (3 pages).

* cited by examiner

*Primary Examiner* — Darwin P Erezo
*Assistant Examiner* — Jing Rui Ou

(57) ABSTRACT

A linear surgical needle is provided having a body portion including a proximal end section; a central section; and a distal end section. The distal end section has a substantially parabolic configuration for producing a substantially uniform stress profile along a length thereof.

5 Claims, 3 Drawing Sheets

UNIFORM STRESS NEEDLE

CROSS REFERENCE TO RELATED APPLICATIONS

This application is a continuation of U.S. patent application Ser. No. 10/620,160 filed Jul. 15, 2003 now U.S. Pat. No. 7,063,716, which claims priority to U.S. Provisional Patent Application Ser. No. 60/396,376 filed Jul. 17, 2002, the disclosures of which are incorporated herein in their entirety by this reference.

TECHNICAL FIELD

The present disclosure relates to surgical needles and, more particularly to surgical needles having a distal taper exhibiting a substantially uniform stress profile which is resistant to a bending load applied thereto.

BACKGROUND OF RELATED ART

Surgical suture needles are well known in the medical arts and include primarily two types of needles, taper point type needles and cutting edge type needles. A taper point type surgical needle includes a proximal end portion defining a suture-mounting portion having a hole or channel to which a suture is to be attached, an intermediate portion defining a main body portion having a generally uniform cross-sectional area throughout an entire length thereof, and a distal end portion defining a tapered portion whose cross-sectional area decreases progressively toward a pointed distal end of the suture needle. Cutting edge type needles also taper to a piercing point, however, unlike taper point type needles, cutting edge type needles include one or more cutting edges with an otherwise smooth outer surface.

In the design of either taper point type or cutting edge type surgical needles it is generally desirable for the needles to exhibit favorable strength and ease of penetration characteristics. It is desirable for a surgical needle to be sufficiently strong in order to penetrate tissue which is being sutured without bending or breaking during a surgical procedure. It is also desirable for the surgical needle to easily penetrate and smoothly pass through the tissue being sutured. The amount of force required for the surgical needle to penetrate tissue includes the force required for the engagement of the tip of the needle with the tissue and the subsequent creation of the entry hole as well as the force required for the widening of the entry hole created. The force required for a taper point type surgical needle to widen the hole is greater than the force required for a cutting edge type needle since the taper point type needle merely dilates the hole and does not cut the hole as would a cutting edge type needle.

Taper point type surgical needles typically have a taper from a middle section of the needle body which ends in a distal piercing point. The taper is often expressed as a ratio of the length of the taper section to the diameter of the wire used to form the needle. It is known that the higher the taper ratio is, the more slender the taper, and thus the resistance to penetration and/or piercing through tissue will typically be lessened. However, the more slender the taper, the mechanical strength for needles manufactured from the same material will be lessened. The converse is also to be expected for needles having lower taper ratios.

In practice, the piercing resistance which the suture needle receives from the tissue of the living body is at a maximum level when the surgical needle is first piercing the skin of the tissue. This is due to the fact that the skin of the tissue has a greater rupture strength than the other parts or layers of the tissue. The resistance of the suture needle as the needle pierces through the skin of the tissue greatly depends on the degree of sharpness of the pointed end of the suture needle. Once the suture needle pierces the skin of the tissue, the piercing resistance is abruptly reduced regardless of the value of the cross-sectional area increase rate of the tapered portion.

In view of the above, it is apparent that the design techniques generally employed to meet the above two design criteria of strength and ease of penetration are often in conflict. As stated above, one approach to improve the strength of a needle is to increase the diameter or thickness of the needle. However, by increasing the thickness of the needle, the force necessary to penetrate the tissue is also increased, and the opening left in the tissue after passage of the needle is also enlarged. Similarly, ease of penetration can be improved by making the needle thinner or more slender. However, a reduction in the thickness of the needle will generally result in a corresponding reduction in the strength of the needle. Thus the design of a needle which exhibits favorable strength and penetration characteristics requires that certain tradeoffs be made in the two criteria to arrive at a needle with optimal overall performance.

Accordingly, there is a continuing need for surgical tapered needles exhibiting improved penetrating characteristics (i.e., resistance to penetration through tissue) and improved mechanical characteristics such as bending strength.

SUMMARY

The present disclosure is directed to a surgical needle having a distal end taper or parabolic profile which exhibits a substantially uniform stress profile when subjected to a load to resist bending thereof.

The surgical needle is intended for use in suturing delicate tissue in conjunction with a plastic, ophthalmologic or reconstructive surgical procedure. The surgical needle includes a taper point profile designed to function as a uniform stress beam and resist bending loads applied to the needle end. The taper point profile is defined by having cross-section diameters which dynamically increase over the length of the needle end. More specifically, the taper point profile of the uniform stress type needle defines a varied taper angle along the length of the needle end with the taper angle decreasing at locations away from the needle point. The taper angles, particularly, adjacent the needle end of the uniform stress type needle are typically substantially greater than corresponding taper angles of a conventional continuous taper point type needle. Thus, the uniform stress type needle defines an enlarged taper point profile relative to conventional taper point type needles. Consequently, the uniform stress type needle is desirably more resistant to breakage.

The cross-section diameters of the taper point profile of the uniform stress type needle are calculated at distances from the needle point using a predetermined maximum allowable stress value. The formula employed for calculating section diameters of the taper point profile is derived from the universal formula for bending stress in a tip loaded cantilever beam. The bending stress at a location along a cantilever beam is directly related to the bending moment and sectional properties at the particular location. Diameters are calculated as a function of the maximum allowable bending stress and the distance from the needle point at specific locations along the taper point profile. The formula for the desired maximum bending stress for circular section properties, and the formula for the bending moment are combined into a formula defining the diameters along the length of a tip loaded round section tapering beam. The resulting formula is as follows:

$$d^3 = [(32W)/(\pi\sigma)]*(X_n)$$

where
    d=measured diameter at location $X_n$;
    W=load normal to the needle;
    $X_n$=distance from a distal-most end of the needle; and
    σ=chosen stress restraint.

The various diameters calculated create a taper point profile which effectively functions as a uniform stress beam. An exception is made in the area or region up to one wire diameter from the needle point to permit a sharper tip angle.

According to one aspect of the present disclosure, a surgical needle is provided having a linear body portion including a proximal end section; a central section; and a distal end section. The distal end section has a substantially parabolic configuration for producing a substantially uniform stress profile along a length thereof. Preferably, the distal end section has a diameter determined according to the equation provided above.

In certain embodiments, the distal end section includes a distal tip having a uniform taper. The distal tip can have a length which is substantially equal to a diameter of the central section of the surgical needle.

It is envisioned that the proximal end section is configured and adapted to secure a suture thereto. The central section can have a rectilinear, circular, oval, triangular, I-beam and/or ribbon shaped cross-sectional profile.

According to another aspect of the present disclosure, a uniform stress needle is provided. The uniform stress needle includes a proximal end section configured and adapted to secure a suture thereto; a central section having a uniform transverse cross-sectional profile; and a distal end section having a parabolic surface profile for producing a substantially uniform stress along a length thereof. Preferably, the surface profile of the distal end section is defined by the equation provided above.

It is envisioned that the distal end section includes a distal tip having a uniform taper. The distal tip preferably has a length which is substantially equal to a diameter of the central section of the needle.

According to yet another embodiment of the present disclosure, a surgical needle is provided including a body portion having a proximal end section; a central section; and a distal end section. The distal end section has a substantially parabolic configuration for producing a substantially uniform stress profile along a length thereof. The distal end section includes a distal tip having a uniform taper.

These and other objects will be more clearly illustrated below by the description of the drawings and the detailed description of the preferred embodiments.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF PREFERRED EMBODIMENTS

Figure 1:
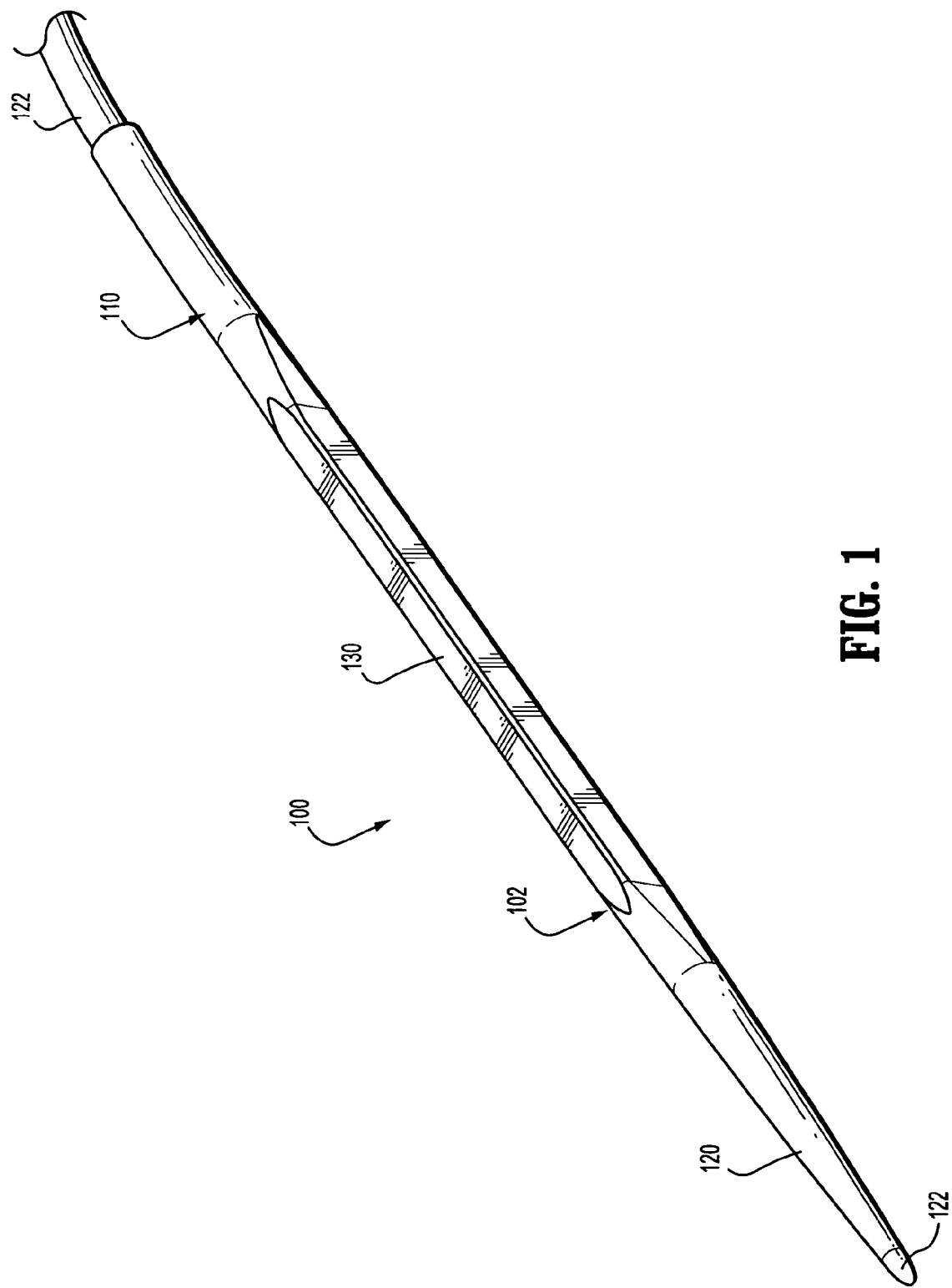
FIG. 1 is a perspective view of a surgical needle in accordance with the present invention.

Preferred embodiments of the presently disclosed surgical needle will now be described in detail with reference to the drawing figures wherein like reference numerals identify similar or identical elements. As used herein, the term "distal" refers to that portion which is further from the user, while the term "proximal" refers to that portion which is closer to the user.

Referring now in detail to FIGS. 1-4, a surgical needle in accordance with the present invention is generally designated with the reference numeral 100. Surgical needle 100 includes a linear body portion 102 having a proximal end section 110, a distal end section 120 and a central section 130. Although FIG. 1 illustrates a straight point type surgical needle, it will be appreciated by those skilled in the art that surgical needle 100 may have other conventional curvatures including compound, ¼, ⅜, ½ or ⅝ type curvatures.

It will be appreciated by those skilled in the art that proximal end section 110 is configured and adapted to receive and hold a surgical suture 112 therein or therethrough. While central section 130 is shown as having a generally rectangular and/or rectilinear cross-section, it is contemplated that central section 130 may have other conventional configurations including circular, oval, triangular, I-beam, ribbon and the like. The cross-sectional profile should be such that a conventional needle grasper can sufficiently grasp and effectively maintain surgical needle 100 in a fixed position as surgical needle 100 penetrates body tissue, thereby preventing the needle from slipping between the jaws of the needle grasper. It is contemplated that central section 130 has a uniform transverse cross-sectional profile.

Figure 2:
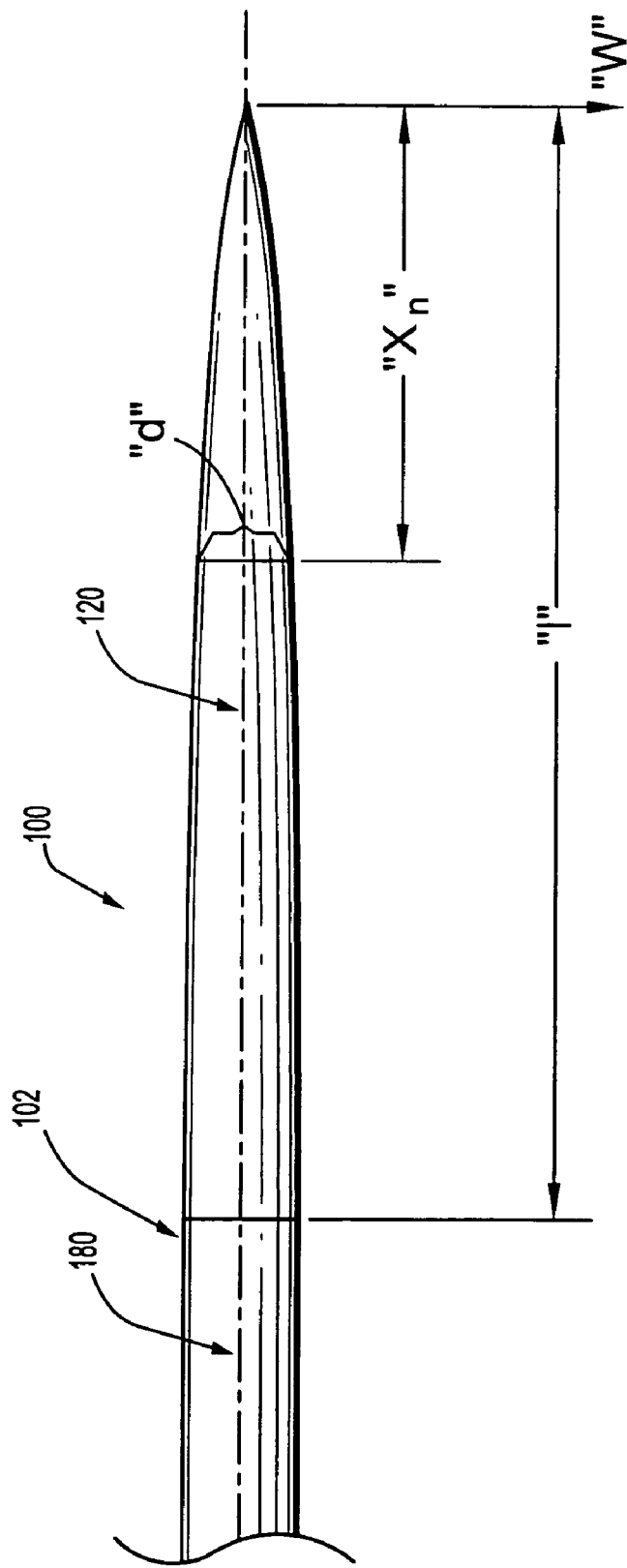
FIG. 2 is a side elevational view of a distal end of the surgical needle shown in FIG. 1.
Figure 3:
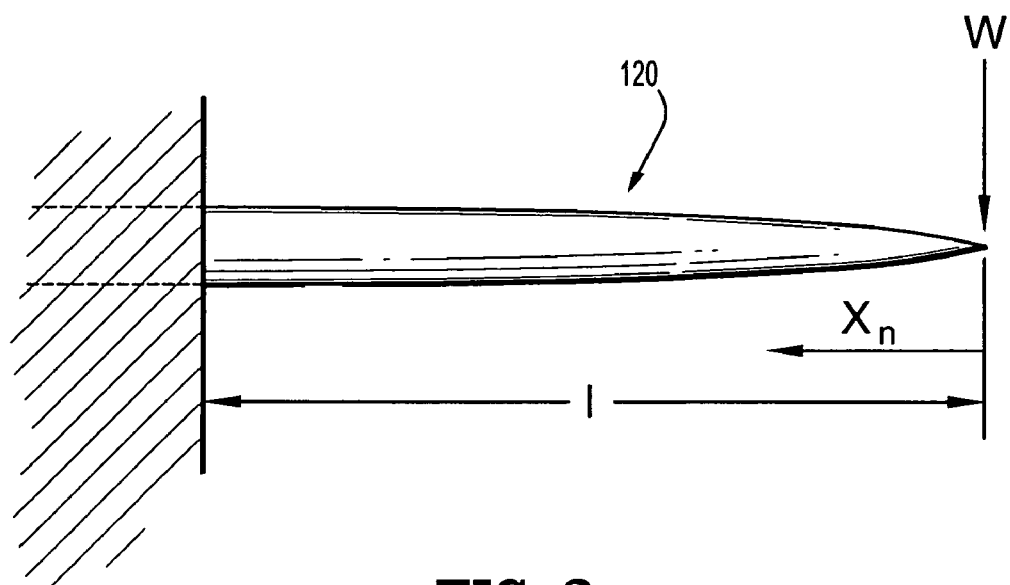
FIG. 3 is a schematic side elevational view of the surgical needle shown in FIG. 1 illustrated as a cantilevered beam.
Figure 4:
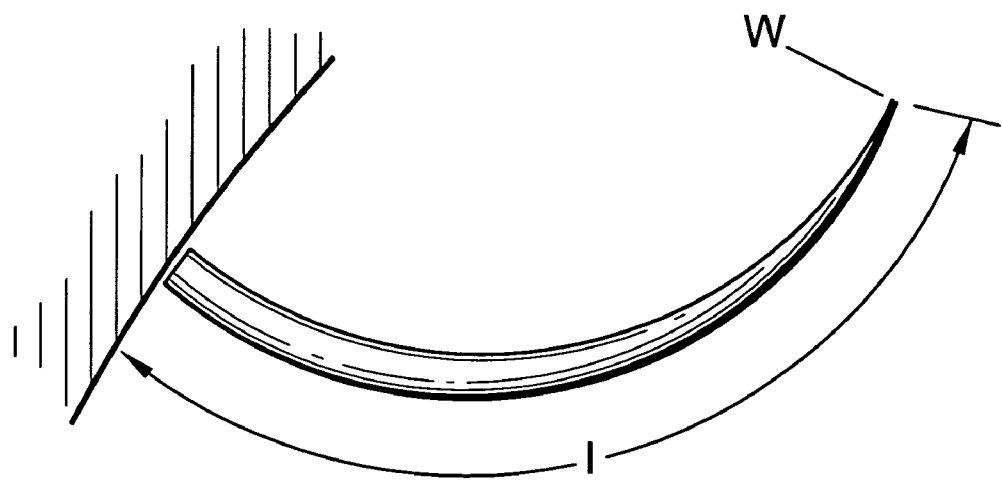
FIG. 4 is a schematic side elevational view of the surgical needle shown in FIG. 1 illustrating the application of a load force at a distal end thereof.

Referring now to FIGS. 2-4, distal end section 120 of surgical needle 100 has a substantially parabolic surface profile for producing a substantially uniform stress profile along its length. The parabolic surface profile of distal end section 120 is determined using known engineering principles. Accordingly, the resulting formula for the cross-sectional diameter of distal end section 120 of surgical needle 100 is as follows:

$$d = (((32W)/(\pi\sigma))*(X_n))^{(1/3)}$$

where
    d=measured diameter at location $X_n$;
    W=load normal to the needle;
    $X_n$=distance from a distal-most end of the needle; and
    σ=chosen stress restraint.

Thus, in accordance with the present disclosure, in a preferred embodiment, the longitudinal cross-sectional profile of distal end section 120 of surgical needle 100 will exhibit a curvature defined by the diametrical equation above. Accordingly, by manufacturing distal end section 120 of surgical needle 100 in accordance with the above diametric equation, distal end section 120 of surgical needle 100 will experience a substantially uniform stress profile along its length.

In other words, as a load, weight and/or force "W" acts on distal end section 120 of needle 100, as seen in FIGS. 2-4, distal end section 120 experiences a substantially uniform stress at each location $X_n$ along its length thereby defining a substantially uniform stress profile along its entire length thereof.

Example

Assuming the following:
Length of the distal end section of the surgical needle=0.3 inches;
Stress=$\sigma$=145,000 p.s.i.; and
Tip Load=W=35 grams at 45° or 0.077 lbs at 45°.

Selected exemplative calculated diameters for the distal end section of the surgical needle appear in the following table.

| Distance from Tip | Distance from Tail | Diameter |
|---|---|---|
| 0.001 | 0.299 | 0.0015548 |
| 0.002 | 0.298 | 0.0019589 |
| 0.003 | 0.297 | 0.0022424 |
| 0.004 | 0.296 | 0.0024681 |
| 0.005 | 0.295 | 0.0026587 |
| 0.006 | 0.294 | 0.0028253 |
| 0.007 | 0.293 | 0.0029742 |
| 0.008 | 0.292 | 0.0031096 |
| 0.009 | 0.291 | 0.0032341 |
| 0.010 | 0.290 | 0.0033497 |
| 0.011 | 0.289 | 0.0034579 |
| 0.012 | 0.288 | 0.0035596 |
| 0.013 | 0.287 | 0.0036559 |
| 0.014 | 0.286 | 0.0037473 |
| 0.015 | 0.285 | 0.0038345 |
| 0.016 | 0.284 | 0.0039179 |
| 0.017 | 0.283 | 0.0039978 |
| 0.018 | 0.282 | 0.0040747 |
| 0.019 | 0.281 | 0.0041488 |
| 0.020 | 0.280 | 0.0042204 |
| 0.021 | 0.279 | 0.0042896 |
| 0.022 | 0.278 | 0.0043566 |
| 0.023 | 0.277 | 0.0044217 |
| 0.024 | 0.276 | 0.0044848 |
| 0.025 | 0.275 | 0.0045463 |
| 0.026 | 0.274 | 0.0046061 |
| 0.027 | 0.273 | 0.0046644 |
| 0.028 | 0.272 | 0.0047213 |
| 0.029 | 0.271 | 0.0047769 |
| 0.030 | 0.270 | 0.0048311 |
| 0.031 | 0.269 | 0.0048842 |
| 0.032 | 0.268 | 0.0049362 |
| 0.033 | 0.267 | 0.0049871 |
| 0.034 | 0.266 | 0.0050370 |
| 0.035 | 0.265 | 0.0050859 |
| 0.036 | 0.264 | 0.0051339 |
| 0.037 | 0.263 | 0.0051810 |
| 0.038 | 0.262 | 0.0052272 |
| 0.039 | 0.261 | 0.0052727 |
| 0.040 | 0.260 | 0.0053174 |
| 0.041 | 0.259 | 0.0053613 |
| 0.042 | 0.258 | 0.0054045 |
| 0.043 | 0.257 | 0.0054471 |
| 0.044 | 0.256 | 0.0054890 |
| 0.045 | 0.255 | 0.0055303 |
| 0.046 | 0.254 | 0.0055709 |
| 0.047 | 0.253 | 0.0056110 |
| 0.048 | 0.252 | 0.0056505 |
| 0.049 | 0.251 | 0.0056895 |
| 0.050 | 0.250 | 0.0057280 |
| 0.051 | 0.249 | 0.0057659 |
| 0.052 | 0.248 | 0.0058033 |
| 0.053 | 0.247 | 0.0058403 |
| 0.054 | 0.246 | 0.0058768 |
| 0.055 | 0.245 | 0.0059129 |
| 0.056 | 0.244 | 0.0059485 |
| 0.057 | 0.243 | 0.0059837 |
| 0.058 | 0.242 | 0.0060185 |
| 0.059 | 0.241 | 0.0060529 |
| 0.060 | 0.240 | 0.0060869 |
| 0.061 | 0.239 | 0.0061205 |
| 0.062 | 0.238 | 0.0061538 |
| 0.063 | 0.237 | 0.0061867 |
| 0.064 | 0.236 | 0.0062192 |
| 0.065 | 0.235 | 0.0062514 |
| 0.066 | 0.234 | 0.0062833 |
| 0.067 | 0.233 | 0.0063149 |
| 0.068 | 0.232 | 0.0063462 |
| 0.069 | 0.231 | 0.0063771 |
| 0.070 | 0.230 | 0.0064078 |
| 0.071 | 0.229 | 0.0064382 |
| 0.072 | 0.228 | 0.0064683 |
| 0.073 | 0.227 | 0.0064981 |
| 0.074 | 0.226 | 0.0065276 |
| 0.075 | 0.225 | 0.0065569 |
| 0.076 | 0.224 | 0.0065859 |
| 0.077 | 0.223 | 0.0066146 |
| 0.078 | 0.222 | 0.0066432 |
| 0.079 | 0.221 | 0.0066714 |
| 0.080 | 0.220 | 0.0066995 |
| 0.081 | 0.219 | 0.0067273 |
| 0.082 | 0.218 | 0.0067548 |
| 0.083 | 0.217 | 0.0067822 |
| 0.084 | 0.216 | 0.0068093 |
| 0.085 | 0.215 | 0.0068362 |
| 0.086 | 0.214 | 0.0068629 |
| 0.087 | 0.213 | 0.0068894 |
| 0.088 | 0.212 | 0.0069157 |
| 0.089 | 0.211 | 0.0069418 |
| 0.090 | 0.210 | 0.0069677 |
| 0.091 | 0.209 | 0.0069934 |
| 0.092 | 0.208 | 0.0070189 |
| 0.093 | 0.207 | 0.0070443 |
| 0.094 | 0.206 | 0.0070694 |
| 0.095 | 0.205 | 0.0070944 |
| 0.096 | 0.204 | 0.0071192 |
| 0.097 | 0.203 | 0.0071439 |
| 0.098 | 0.202 | 0.0071683 |
| 0.099 | 0.201 | 0.0071926 |
| 0.100 | 0.200 | 0.0072168 |
| 0.101 | 0.199 | 0.0072407 |
| 0.102 | 0.198 | 0.0072646 |
| 0.103 | 0.197 | 0.0072882 |
| 0.104 | 0.196 | 0.0073117 |
| 0.105 | 0.195 | 0.0073351 |
| 0.106 | 0.194 | 0.0073583 |
| 0.107 | 0.193 | 0.0073814 |
| 0.108 | 0.192 | 0.0074043 |
| 0.109 | 0.191 | 0.0074271 |
| 0.110 | 0.190 | 0.0074497 |
| 0.111 | 0.189 | 0.0074722 |
| 0.112 | 0.188 | 0.0074946 |
| 0.113 | 0.187 | 0.0075168 |
| 0.114 | 0.186 | 0.0075390 |
| 0.115 | 0.185 | 0.0075609 |
| 0.116 | 0.184 | 0.0075828 |
| 0.117 | 0.183 | 0.0076045 |
| 0.118 | 0.182 | 0.0076261 |
| 0.119 | 0.181 | 0.0076476 |
| 0.120 | 0.180 | 0.0076690 |

As seen in FIG. 1, it is contemplated that distal end section 120 of surgical needle 100 includes a distal tip 122 having a profile which defines a tip having a sharper angle than the tip defined by the diametrical equation presented above. In particular, it is envisioned that distal tip 122 has a uniform taper (i.e., a uniform and/or a non-parabolic surface profile). It is further contemplated that the sharper angle of distal tip 122 has a length which is substantially equal to one wire diameter (i.e., the diameter of the intermediate body portion of surgical needle).

It will be understood that various modifications may be made to the embodiments described herein. Therefore the above description should not be construed as limiting, but merely as exemplifications of preferred embodiments. Those skilled in the art will envision other modifications within the scope and spirit of the claims appended hereto.

The invention claimed is:

1. A surgical needle, comprising:
 a proximal end section configured and adapted to secure a suture thereto;
 a central section having a substantially uniform transverse cross-sectional profile; and
 a distal end section having a substantially parabolic surface profile for producing a substantially uniform stress along a length thereof, the surface profile being defined by the following equation:

$$d=(((32W)/(\pi\sigma))*(X_n))^{(1/3)}$$

where
 $d$=measured diameter at location $X_n$;
 $W$=load normal to the needle;
 $X_n$=distance from a distal-most end of the needle; and
 $\sigma$=chosen stress restraint,
wherein the central section has a cross-sectional profile selected from the group consisting of rectilinear, circular, triangular, I-beam, and ribbon shaped cross-sectional profiles.

2. The surgical needle of claim 1, wherein the distal end section includes a distal tip having a substantially uniform taper.

3. The surgical needle of 2, wherein the distal tip has a length which is substantially equal to a diameter of the central section of the needle.

4. The surgical needle of claim 2, wherein the proximal end section is configured and adapted to secure a suture thereto.

5. A surgical needle, comprising:
 a proximal end section configured and adapted to secure a suture thereto;
 a central section having a substantially uniform transverse cross-sectional profile; and
 a distal end section having a substantially parabolic surface profile for producing a substantially uniform stress along a length thereof, the distal end section having a cross-section defining a circle, the surface profile being defined by the following equation:

$$d=(((32W)/(\pi\sigma))*(X_n))^{(1/3)},$$

where
 $d$=measured diameter at location $X_n$;
 $W$=load normal to the needle;
 $X_n$=distance from a distal-most end of the needle; and
 $\sigma$=chosen stress restraint,
wherein the central section has a cross-sectional profile selected from the group consisting of rectilinear, circular, triangular, I-beam, and ribbon shaped cross-sectional profiles.

* * * * *